United States Patent [19]

Yamada et al.

[11] Patent Number: 4,563,426

[45] Date of Patent: Jan. 7, 1986

[54] PROCESS FOR PRODUCING BIOTIN-VITAMERS

[75] Inventors: Hideaki Yamada; Yoshiki Tani, both of Kyoto; Yoshikazu Izumi, Hirakata, all of Japan

[73] Assignee: Nippon Zeon Co., Ltd., Tokyo, Japan

[21] Appl. No.: 505,124

[22] Filed: Jun. 21, 1983

Related U.S. Application Data

[63] Continuation of Ser. No. 260,885, May 6, 1981, abandoned.

[30] Foreign Application Priority Data

May 15, 1980 [JP] Japan .................................. 55-64425

[51] Int. Cl.[4] .......................... C12P 17/18; C12N 1/38
[52] U.S. Cl. ..................................... 435/119; 435/244
[58] Field of Search ................................ 435/119, 244

[56] References Cited

U.S. PATENT DOCUMENTS 3,859,167  1/1975  Ogino et al. ........................ 435/119

OTHER PUBLICATIONS

Ogata et al., Agr. Biol. Chem., vol. 29, No. 10, pp. 889–894 (1965).

*Primary Examiner*—Alvin E. Tanenholtz
*Attorney, Agent, or Firm*—Sherman and Shalloway

[57] ABSTRACT

In a process which comprises cultivating a microorganism having the ability to produce a biotin-vitamer in a culture medium in the presence of a biotin-vitamer precursor thereby to produce the biotin-vitamer and accumulate it in the culture medium, the improvement wherein the biotin-vitamer precursor is added to the culture medium after the microbial cells have been grown.

4 Claims, No Drawings

PROCESS FOR PRODUCING BIOTIN-VITAMERS

This application is a continuation of application Ser. No. 260,885, filed May 6, 1981, now abandoned.

This invention relates to an improvement in a process for producing biotin-vitamers using microorganisms.

Biotin-vitamers are vitamins necessary for animals, plants and microorganisms. For production of biotin-vitamers using microorganisms, a method which comprises adding to a culture medium a biotin-vitamer precursor such as pimelic acid and desthiobiotin before the growth of the microbial cells has been known [K. Ogata et al., Argic. Biol. Chem. 29, 889 (1965)]. This method, however, is not economical because the amount of biotin-vitamers produced and accumulated is very small. This is due reportedly to the strong feedback repression of biotin [Y. Izumi, and K. Ogata, Adv. Appl. Microbiol. 22, 155–157 (1977); C. H. Pai and H. C. Lichstein, Biochim. Biophys. Acta 100, 36 (1965)].

It is an object of this invention therefore to provide a process by which biotin-vitamers can be produced and accumulated in high yields by avoiding this feedback repression.

According to this invention, there is provided a process which comprises cultivating a microorganism having the ability to produce a biotin-vitamer in a culture medium in the presence of a biotin-vitamer precursor to produce the biotin-vitamer and accumulate it in the culture medium, characterized in that the biotin-vitamer precursor is added to the culture medium after the microbial cells have been grown.

The biotin-vitamer produced in the present invention consists mainly of desthiobiotin, biotin and biotin sulfoxide. It also contains diaminobiotin, biotinamide and pelargonic acids such as diaminopelargonic acid. These biotin-vitamers are generally called total biotin, and can be quantitatively determined by a method using *Saccharomyces cerevisiae* ATCC 7754.

The microorganisms used in the present invention are microorganisms having the ability to produce biotin-vitamers, namely microorganisms having an enzyme system for biosynthesis of biotin-vitamers. Specific examples include microorganisms of the genus Bacillus, such as *Bacillus sphaericus* IFO 3525; microorganisms of the genus Chromobacterium, such as *Chromobacterium iodinum* IFO 3558; microorganisms of the genus Pseudomonas such as *Pseudomonas taetrolens* IFO 3460; microorganisms of the genus Arthrobacter, such as *Arthrobacter ureafaciens*; microorganisms of the genus Brevibacterium, such as *Brevibacterium* sp.; and microorganisms of the genus Agrobacterium, such as *Agrobacterium* sp. The microorganisms of the genus Bacillus are especially preferred. Natural and artificial variants and mutants of these microorganisms can also be used so long as they have the ability to produce biotin-vitamers.

The "biotin-vitamer precursor", as used in the present invention, denotes a precursor of the desired biotin-vitamer. The type of the precursor used varies depending upon the type of the product desired. For example, when the final product is biotin, desthiobiotin is also included within the precursors. But when desthiobiotin is the desired product, it is naturally excluded from the precursors. Specific examples of the precursor are pimelic acid, azelaic acid, and desthiobiotin. Pimelic acid and desthiobiotin are preferred. Pimelic acid is most frequently used.

Carbon sources used in the culture medium in accordance with this invention include, for example, carbohydrates such as starches and sugars, alcohols such as glycerol, and hydrocarbons such as kerosene. Nitrogen sources include, for example, organic materials such as peptone, Casamino acid, yeast extracts, amino acids, defatted soybeans, corn steep liquor, meat extract and urea, and inorganic substances such as ammonium salts and nitrate salts and various metal salts.

In the present invention, usual shaking cultivation or aerobic stirred cultivation can be used.

The time of addition of the biotin-vitamer precursor may be any time after the microorganism has been cultivated and its cells have grown. Desirably, it is after an enzyme system for biosynthesis of biotin in the microbial cells has been formed sufficiently, that is, one to two days after the starting of the cultivation. This is not particularly restrictive, however, since the optimum time of addition differs depending upon the types of the microorganism and the biotin precursor.

The suitable cultivation temperature is 20° to 40° C. It is desirable to select temperatures which are suitable for the formation of the enzyme system of biotin biosynthesis and which do not easily cause feed back repression by the resulting biotin, i.e. generally not more than 30° C., particularly 28° to 30° C., in the cell growing period, and temperatures which are suitable for enzyme reaction, i.e. generally temperatures above 30° C., particularly 35° to 40° C., in the enzyme reaction period after the addition of the precursor.

The following examples illustrate the present invention further.

The biotin-vitamers (total biotin) produced and accumulated were quantitatively determined by a method using *Sacchromyces cerevisiae*. Furthermore, biotin (true biotin) produced and accumulated was quantitatively determined by a microorganism determination method using *Lactobacillus plantarum* ATCC 8014.

EXAMPLE 1

| Composition of a culture medium | |
|---|---|
| Glycerol | 20 g |
| Proteose.peptone (a product of Difco Laboratories) | 50 g |
| Casamino acid (vitamin-free) | 5 g |
| $K_2HPO_4$ | 1 g |
| KCl | 0.5 g |
| $MgSO_4.7H_2O$ | 0.5 g |
| $FeSO_4.7H_2O$ | 0.01 g |
| $MnSO_4.4\text{-}6H_2O$ | 0.01 g |
| Thiamine hydrochloride | 20 μg |
| Distilled water | 1000 ml |

Four ml of the culture medium (pH 7.0) of the above composition was put in a test tube having a diameter of 16 mm, and sterilized at 120° C. for 10 minutes. A platinum loopful of *Bacillus sphaericus* IFO 3525 was inoculated in the medium and cultivated for 4 days under shaking at 200 rpm. As a precursor, 0.1 ml of a sterilized aqueous solution of pimelic acid (40 mg/ml) was added to the culture medium before the cultivation, one day after the cultivation, or two days after the cultivation, respectively. The cultivation temperature was 30° C. before the precursor was added, and 30° C. or 37° C. respectively after the addition of the precursor. When the precursor was added before the cultivation, the shaking cultivation was performed for one day at 30° C., and then for 3 days at 30° C. or 37° C. under shaking.

The amounts of biotin-vitamers (total biotin) and biotin (true biotin) accumulated were as shown in Table 1.

TABLE 1

| Time of addition of pimelic acid | Cultivation temperature after the addition of pimelic acid (°C.) | Amount of total biotin accumulated (μg/ml) | Amount of true biotin accumulated (μg/ml) |
| --- | --- | --- | --- |
| Before cultivation | 30 | 10 | 0.1 |
|  | 37 | 11 | 0.2 |
| One day after the cultivation | 30 | 21 | 2.2 |
|  | 37 | 49 | 3.5 |
| Two days after the cultivation | 30 | 52 | 0.4 |
|  | 37 | 70 | 0.7 |

It is clearly seen from Table 1 that by adding pimelic acid after the cultivation, the amounts of total biotin and true biotin accumulated increased markedly. This tendency was especially outstanding when the cultivation temperature was increased to 37° C. after the addition of pimelic acid.

EXAMPLE 2

The same experiment as shown in Example 1 was conducted except that the same amount of a sterilized aqueous solution of DL-desthiobiotin (4 mg/ml) was used instead of the sterilized aqueous solution of pimelic acid (40 mg/ml) used in Example 1. The amount of true biotin accumulated was as shown in Table 2.

TABLE 2

| Time of addition of DL-desthiobiotin | Cultivation temperature after the addition of DL-desthiobiotin (°C.) | Amount of true biotin accumulated (μg/ml) |
| --- | --- | --- |
| Before the cultivation | 30 | 0.1 |
|  | 37 | 0.2 |
| One day after the cultivation | 30 | 1.2 |
|  | 37 | 2.0 |
| Two days after the cultivation | 30 | 0.3 |
|  | 37 | 0.8 |

What we claim is:

1. In a process which comprises cultivating a strain of the genus Bacillus having the ability to produce a biotin-vitamer in a nutrient-containing culture medium in the presence of pimelic acid thereby to produce the biotin-vitamer and accumulate it in the culture medium, the improvement wherein pimelic acid is added to the culture medium one to two days after the starting of the cultivation.

2. The process of claim 1 wherein biotin is obtained as the biotin-vitamer.

3. The process of claim 1 wherein the cultivation temperature during the cell growing period is in the range of from 28° to 30° C., and the cultivation temperature in the enzyme reaction period after the addition of pimelic acid is from 35° to 40° C.

4. The process of claim 3 wherein biotin is obtained as the biotin-vitamer.

* * * * *